United States Patent
Schuetz

(10) Patent No.: US 10,633,266 B2
(45) Date of Patent: Apr. 28, 2020

(54) UV LIGHT REACTOR FOR CONTAMINATED FLUIDS

(71) Applicant: Reinhard Schuetz, Calgary (CA)

(72) Inventor: Reinhard Schuetz, Calgary (CA)

(73) Assignee: UV-DOX PATENT INC., Calgary (CA)

( * ) Notice: Subject to any disclaimer, the term of this patent is extended or adjusted under 35 U.S.C. 154(b) by 0 days.

(21) Appl. No.: 15/924,255

(22) Filed: Mar. 18, 2018

(65) Prior Publication Data

US 2018/0265382 A1    Sep. 20, 2018

(30) Foreign Application Priority Data

Mar. 20, 2017    (CA) ...................................... 2961429

(51) Int. Cl.
*C02F 1/72* (2006.01)
*C02F 1/32* (2006.01)
(Continued)

(52) U.S. Cl.
CPC ................ *C02F 1/725* (2013.01); *A61L 2/10* (2013.01); *A61L 9/205* (2013.01); *B01D 53/86* (2013.01);
(Continued)

(58) Field of Classification Search
CPC .... C02F 1/725; C02F 1/325; C02F 2101/322; C02F 2301/028; C02F 2201/324; C02F 2201/3223; C02F 2101/327; C02F 2305/10; C02F 2201/328; C02F 2303/04; B01D 53/8668; B01D 53/86; B01D 2257/91;
(Continued)

(56) References Cited

U.S. PATENT DOCUMENTS 4,798,702 A    1/1989  Tucker
4,956,754 A    9/1990  Chen
(Continued)

OTHER PUBLICATIONS

WO2016020694, Nov. 2016, Clarke, Henderson (Year: 2016).*

*Primary Examiner* — Sean E Conley
*Assistant Examiner* — Brendan A Hensel
(74) *Attorney, Agent, or Firm* — W & C IP; Thomas E. Malyszko

(57) ABSTRACT

An apparatus for treating a contaminated fluid has a UV lamp within a tubular housing. A plurality of baffles within the housing create meandering pathways parallel to the lamp for exposing the fluid to the UV light along the entire length of the pathways. A photocatalytic coating on the baffles and inner surfaces of the housing is maintained within a pre-set radial distance, preferably no more than about 75 mm, from the lamp for optimal creation of a photocatalytic reactant. The contaminated fluid flowing through the meandering pathways is maintained in close proximity to the lamp and has adequate time for exposure to the ultraviolet light and photocatalytic reactant for treatment before exiting the housing. The baffles are removably positioned within the housing for convenient maintenance or to alter the length of the pathways, without re-sizing the housing. This apparatus is considered an affordable and compact environmental protection device capable of "redefining pollution control" by potentially mitigating close to 100% of harmful bacteria and toxic compounds.

20 Claims, 9 Drawing Sheets

FIG. 1

(51) Int. Cl.
  *B01J 21/06* (2006.01)
  *B01J 35/00* (2006.01)
  *A61L 9/20* (2006.01)
  *B01D 53/86* (2006.01)
  *B01J 37/02* (2006.01)
  *A61L 2/10* (2006.01)
  *C02F 101/32* (2006.01)

(52) U.S. Cl.
  CPC ........ *B01D 53/8668* (2013.01); *B01J 21/063* (2013.01); *B01J 35/004* (2013.01); *B01J 37/0225* (2013.01); *C02F 1/325* (2013.01); B01D 2255/20707 (2013.01); B01D 2255/802 (2013.01); B01D 2257/708 (2013.01); B01D 2257/91 (2013.01); B01D 2259/804 (2013.01); C02F 2101/322 (2013.01); C02F 2101/327 (2013.01); C02F 2201/324 (2013.01); C02F 2201/328 (2013.01); C02F 2201/3223 (2013.01); C02F 2301/028 (2013.01); C02F 2303/04 (2013.01); C02F 2305/10 (2013.01)

(58) Field of Classification Search
  CPC ........ B01D 2259/804; B01D 2257/708; B01D 2255/20707; B01D 2255/802; A61L 9/205; A61L 2/10; B01J 35/004; B01J 21/063
  See application file for complete search history.

(56) References Cited

U.S. PATENT DOCUMENTS

| | | | |
|---|---|---|---|
| 5,004,541 A | | 4/1991 | Noll et al. |
| 5,069,782 A | | 12/1991 | Moyer, Jr. et al. |
| 5,069,885 A | * | 12/1991 | Ritchie ............... B01J 16/005 422/186 |
| 5,501,801 A | | 3/1996 | Zhang et al. |
| 6,932,947 B2 | | 8/2005 | Leung |
| 9,260,323 B2 | * | 2/2016 | Boodaghians ........ C02F 1/325 |
| 2002/0069626 A1 | * | 6/2002 | Fiacco ............... B01D 45/14 55/400 |
| 2007/0084350 A1 | | 4/2007 | Parker et al. |
| 2009/0041632 A1 | | 2/2009 | Day et al. |
| 2009/0145855 A1 | | 6/2009 | Day et al. |
| 2010/0150793 A1 | * | 6/2010 | Chan ................... A61L 2/10 422/186.3 |
| 2011/0300230 A1 | * | 12/2011 | Peterson ............ B01D 61/58 424/600 |
| 2017/0225973 A1 | * | 8/2017 | Henderson ........... B08B 1/008 |

* cited by examiner

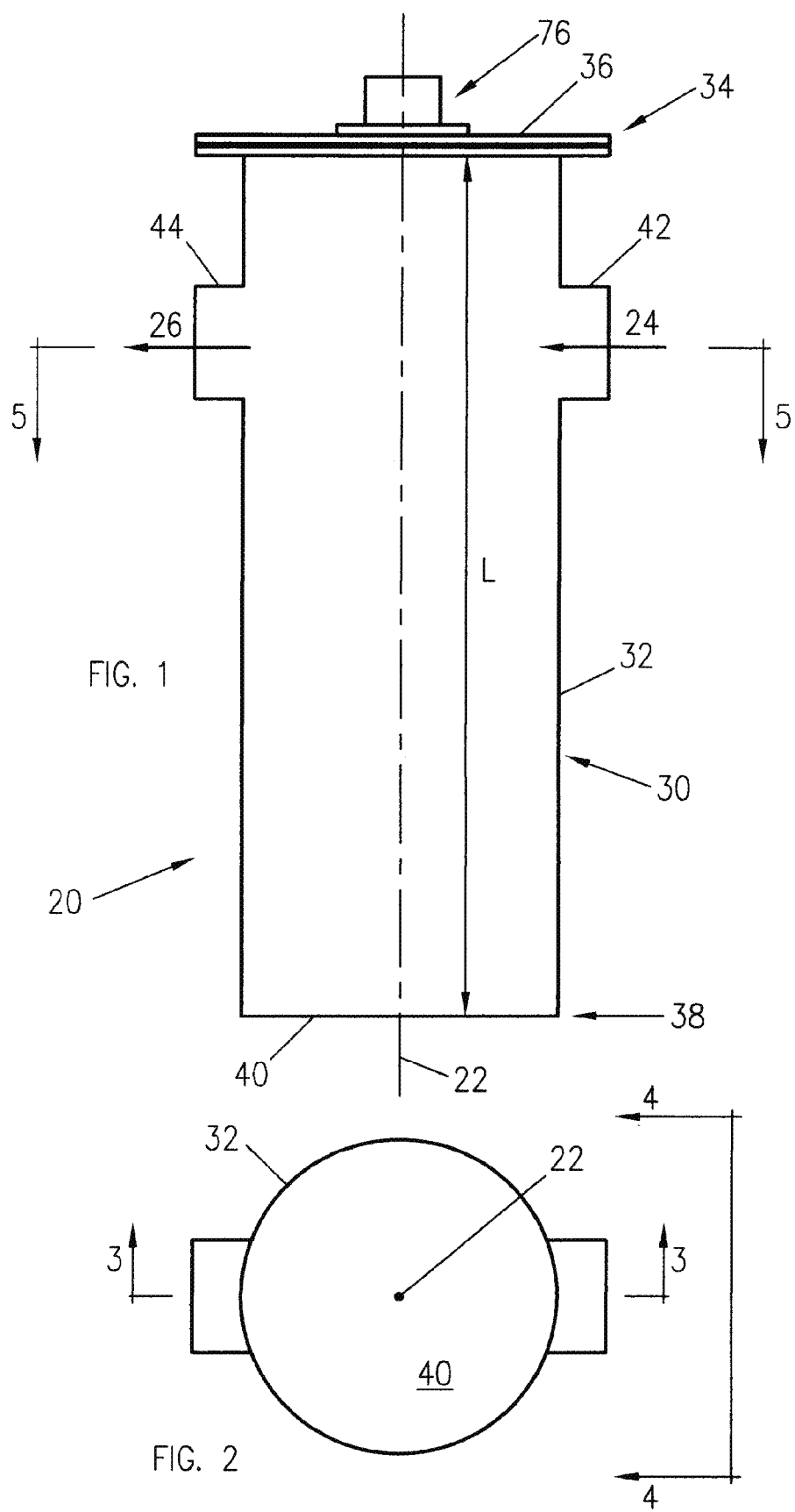

UV LIGHT REACTOR FOR CONTAMINATED FLUIDS

FIELD OF THE INVENTION

The present invention relates to a compact apparatus and method of treating contaminated fluids, and in particular to treating such fluids using an energy source, such as UV light, and a photocatalytic reactant to cost effectively target and destroy harmful chemical compounds and biological organisms therein.

BACKGROUND OF THE INVENTION

We continue to suffer the negative health effects of pollution in our environment. Although large scale pollution sources, or emitters, appear to be targeted by stricter regulations, widespread and harmful contamination from individual small scale emitters seems largely ignored, yet cumulatively has a significant environmental impact.

An example of small emitters are retail gasoline fuelling station tanks. Based on Canadian Government statistics, the operational evaporative losses from these fuelling stations alone amount to almost 40 million litres per year, which include highly carcinogenic benzene. By extrapolation evaporative losses of about 400+ million litres yearly could be emitted in the United States of America. Therefore, even though small emissions from individual sources (such as from a single gasoline storage tank or soil remediation process) may be viewed as insignificant, implementation of fugitive emission control is imperative for these small emitters to reduce cumulative effect. Unfortunately fugitive emission controls for small emitters are currently lacking, and so the present invention is geared to target this market.

It is known that certain types of ultraviolet (hereinafter "UV") light can destroy harmful chemical compounds and biological organisms, rendering them virtually harmless and inert. It is believed that organisms are typically prevented from reproducing through destruction of their DNA when exposed to UVC light, while higher UV generated forms of energy can break down bonds of chemical compounds and transform them into environmentally benign substances.

Prior art designs exist that create pathways for fluids (namely gases and/or liquids) and provide a UV light with the intention of treating those fluids as they pass along the pathway. One example of a pathway created with a baffle or tube arrangement is shown in U.S. Pat. No. 5,004,541 (Noll et al.). However, this patent lacks features critical to effective treatment of fluids, and the types of pathways shown are not optimal for, or are incapable of, exposing the fluid to a desired level of UV light for destruction of both harmful biological organisms and toxic chemical compounds.

Other prior art designs incorporate desirable photoreactive coatings to increase the effectiveness of UV light treatment of contaminated fluids, but again the pathway designs result in sub-optimal exposure to a desired level of UV light, and the surface coatings are not optimized for cost efficient commercial implementation. Some examples are U.S. Pat. No. 5,069,885 (Ritchie) and US patent application 2009/0145855 (Day et al.).

What is therefore desired is a novel apparatus and method for treating contaminated fluids which overcomes the limitations and disadvantages of the existing designs. Preferably, it should provide a single source solution to combat not only harmful biological organisms, but also environmental contamination perpetuated by toxic and noxious aromatic chemical compounds emitted from small scale emitters. It should provide a cost effective compact enclosure complete with inlet/outlet connections, an energy source such as a UV lamp, internal Titanium Dioxide ($TiO_2$) photocatalytic coating (or equivalent photocatalyst), and a specially designed internal baffle system that is removably positioned within the apparatus for ease of removal and alteration if need be. The combination of these features should not only allow for continuous and extended fluid exposure to UV light within the enclosure, but should also confine the maximum distance from the lamp to all internal enclosure coated surfaces in order to achieve a highly effective photocatalytic reaction. In addition, the present invention should also allow for sequential or parallel joining of numerous UV light reactors to achieve increased volume treatment of contaminated fluids entrained either with harmful bacteria, toxic chemicals or noxious aromatic elements.

SUMMARY OF THE PRESENT INVENTION

According to the present invention, there is provided in one aspect an apparatus for treatment of a contaminated fluid comprising:

a tubular housing having an outer wall fluidly sealed at each end, and having an inlet and an outlet, wherein said inlet receives said contaminated fluid and creates at least one fluid stream thereof;

an energy source located centrally along the length of said housing [for emitting ultraviolet light];

a plurality of baffles arranged in a spaced relationship circumferentially about said energy source, each of said baffles extending radially between said energy source and said housing outer wall, and extending longitudinally between said housing ends, each baffle forming an opening at one end thereof, wherein said openings in adjacent baffles are located at opposed ends of said housing thereby creating a meandering pathway parallel to said energy source for said fluid stream from said inlet to said outlet to provide uninterrupted exposure to energy emitted from said energy source along the length of said pathway; and, a photocatalytic coating on at least said baffles and inner surfaces of said housing's outer wall within a pre-set radial distance of said energy source for exposure to said energy to activate a photocatalytic reactant, so that said contaminated fluid flowing through said meandering pathway is continuously maintained in close proximity to said energy source and is provided adequate time for combined exposure to said energy and said photocatalytic reactant to treat said fluid before exiting said housing through said outlet.

BRIEF DESCRIPTION OF THE DRAWING FIGURES

Embodiments of the invention will now be described, by way of example only, with reference to the accompanying drawings, wherein:

FIG. 1 is a side view of the exterior of a UV light reactor according to a preferred embodiment of the present invention showing the reactor in an upright "operational" position with the inlet and outlet ready for fluid connections;

FIG. 2 is an end view from below of the reactor of FIG. 1;

DESCRIPTION OF PREFERRED EMBODIMENTS

Figure 3:
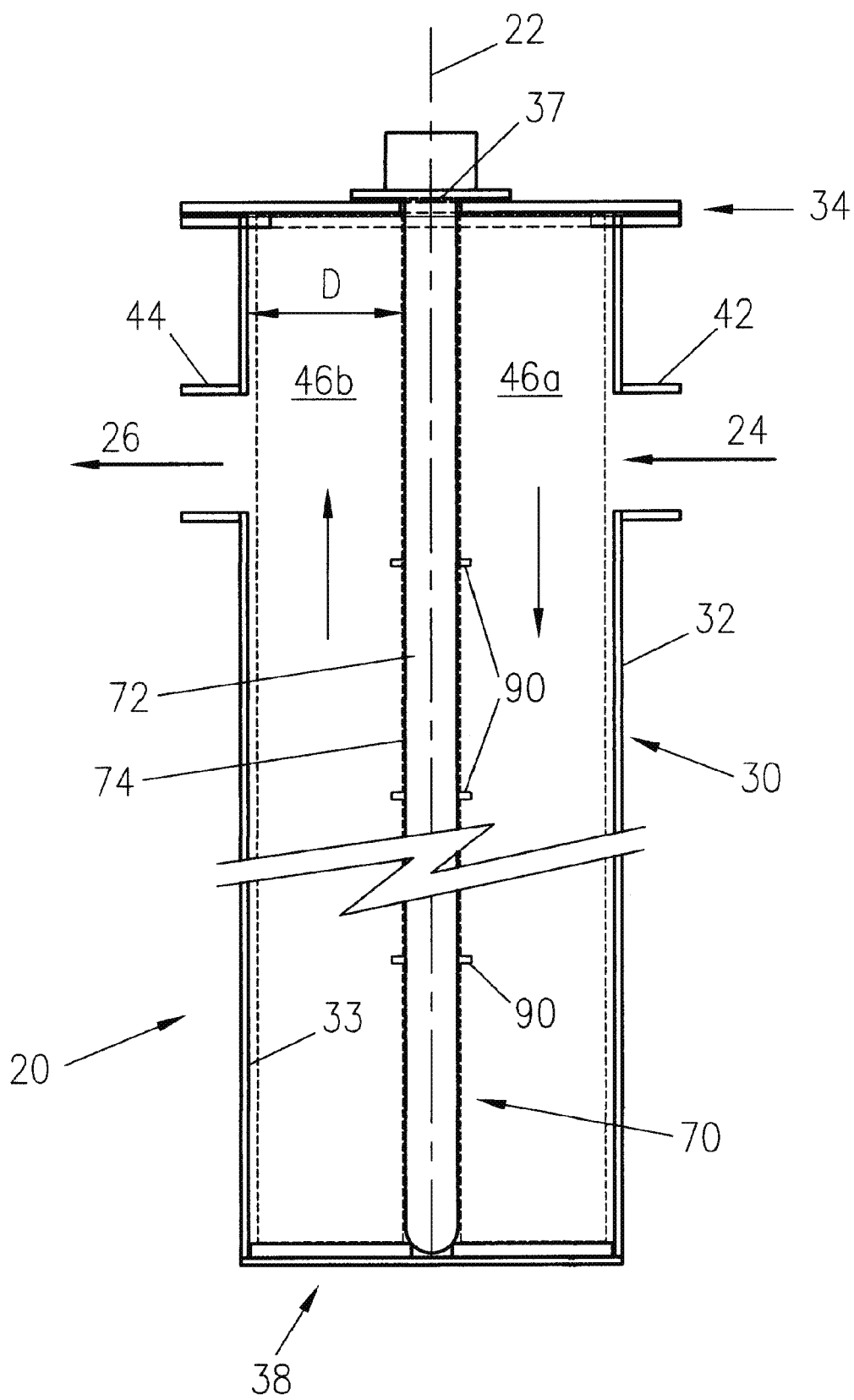
FIG. 3 is a cross-sectional view along the line 3-3 of FIG. 2.

The figures show a UV light reactor (generally designated by reference numeral 20) having a hollow tubular container 30 for housing an energy source, such as an elongate lamp arrangement 70 mounted generally centrally along a longitudinal axis 22 thereof. The purpose of the lamp arrangement is to emit energy in the form of ultraviolet light, or radiation (typically referred to as "UV light"), inside the container along its length, for treating incoming contaminated fluid 24 before it is discharged as treated fluid (arrow 26).

The container 30 has a housing formed by a cylindrical outer wall 32 which is fluidly sealed at its opposed ends, namely at a first (or top) end 34 by a lid assembly 36, and at a second (or bottom) end 38 by a circular end plate 40. Depending on the type of contaminated fluid being treated, preferred materials for the container include aluminum and stainless steel. It is anticipated that in use the reactor 20 will typically be oriented horizontally, namely rotated 90 degrees to the upright position shown in FIG. 1, but advantageously any orientation is suitable for operation of the device. Nonetheless, terms such as "top" or "bottom", "left" or "right", and the like will be used for ease of identifying certain features of the reactor in the orientation shown in the figures. Employment of these terms is not intended to limit the reactor's orientation in use. Further, when describing the invention, all terms not defined herein have their common art-recognized meaning.

In the preferred embodiment of the reactor the container's outer wall 32 has an inlet 42 configured to be operatively coupled in a fluid tight manner to a supply (not shown) of contaminated fluid 24, and has a radially opposed outlet 44 for discharge of fluid after treatment within the reactor. The supply delivers the fluid to the inlet either by mechanical means (e.g. pump, fan, suction, etc) or non-mechanical means (e.g. gravity, evaporation, etc). The inlet and outlet are both shown as round, as that is most typically the shape the piping to which they will be coupled, either by threaded connection, clamping, flanging or such, but they may take any form most suitable to the operational environment. In the configuration shown there is a single inlet and a divider plate 46 (best seen in FIG. 5) for splitting the incoming fluid flow 24 into two streams 24a ("left" stream) and 24b ("right" stream). The streams are split generally equally in this embodiment, to suit the symmetry of the reactor's internal flow pattern and capacities (as will be described shortly) and the location of the fluid outlet 44 opposite the inlet. In the FIG. 5 version both fluid streams 24a, 24b are eventually directed by another divider plate 46[1] to the outlet 44 where they join into the singular discharged fluid stream 26. However, it will be appreciated that the fluid streams 24a and 24b may be split in different proportions to suit the internal structure of the reactor. The incoming flow 24 might also be proportioned upstream of the reactor to arrive in separate streams, and thus the inlet 42 may be configured to be two or more ports at appropriate positions on the outer wall 32. Likewise, the outlet 44 may take the form of two or more ports if need be. Alternately, the incoming fluid flow 24 need not be split but maintained as a single fluid stream to the outlet 44, but such embodiment is not preferred since it may require location of the fluid outlet beside the inlet, which could pose problems when coupling to external piping or equipment.

The reactor's energy source is a lamp arrangement 70 having an elongate lamp 72 for emitting UV light (sometimes referred to herein as a "UV lamp"). In the preferred embodiment UVC light is desired, and thus a "UVC lamp" 72 is provided along the reactor's central longitudinal axis 22, extending substantially along the length of the container 30 between the first and second ends 34, 38. The UVC lamp is housed within a clear and fluid tight tubular sleeve 74, such as those made of high quality quartz, to avoid contact with fluid from the reactor when mounted therein. Instead of or in addition to the sleeve, the lamp 72 may be covered in a tight fitting clear Teflon (or equivalent material) to prevent fluid contact and avoid personal injury in case of lamp breakage when being handled by an operator. The lamp and sleeve are supported from the lid 36 at the top end 34 of the container, and may optionally have some support at the bottom end 38. In the FIG. 4 embodiment the top end of the lamp and sleeve are fixed to a mounting assembly 76 which, after the lamp and sleeve are inserted into the container through a hole 37 in the lid assembly 36, has a flange for forming a fluid seal about the hole 37, with the aid of a gasket 78 or the like if needed. The mounting assembly 76 is preferably removably secured to the lid 36 via appropriate means such as a threaded connection with the hole 37 or by fastening the flange to the lid, so that an operator may readily remove the lamp from the container for cleaning the sleeve, replacing the UVC lamp, or other maintenance. It will be appreciated that the lamp's mounting assembly 76 may be permanently connected to the lid 36, thus requiring removal of the lid for access to the lamp, but such arrangement is less convenient and thus not preferred. The mounting assembly 76 is operatively coupled to a source of power (not shown).

Figure 4:
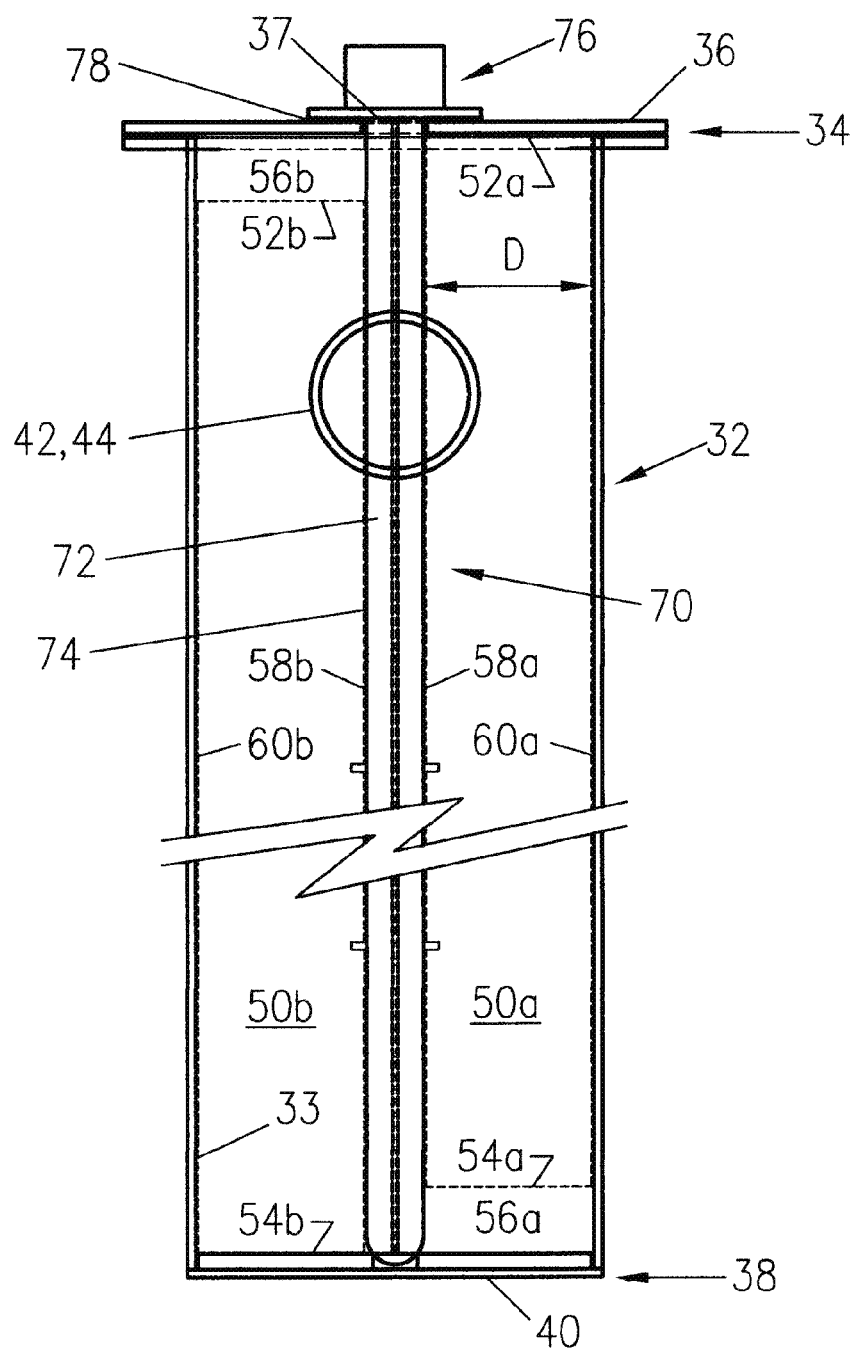
FIG. 4 is a transparent side view from the line 4-4 of FIG. 2.
Figure 5:
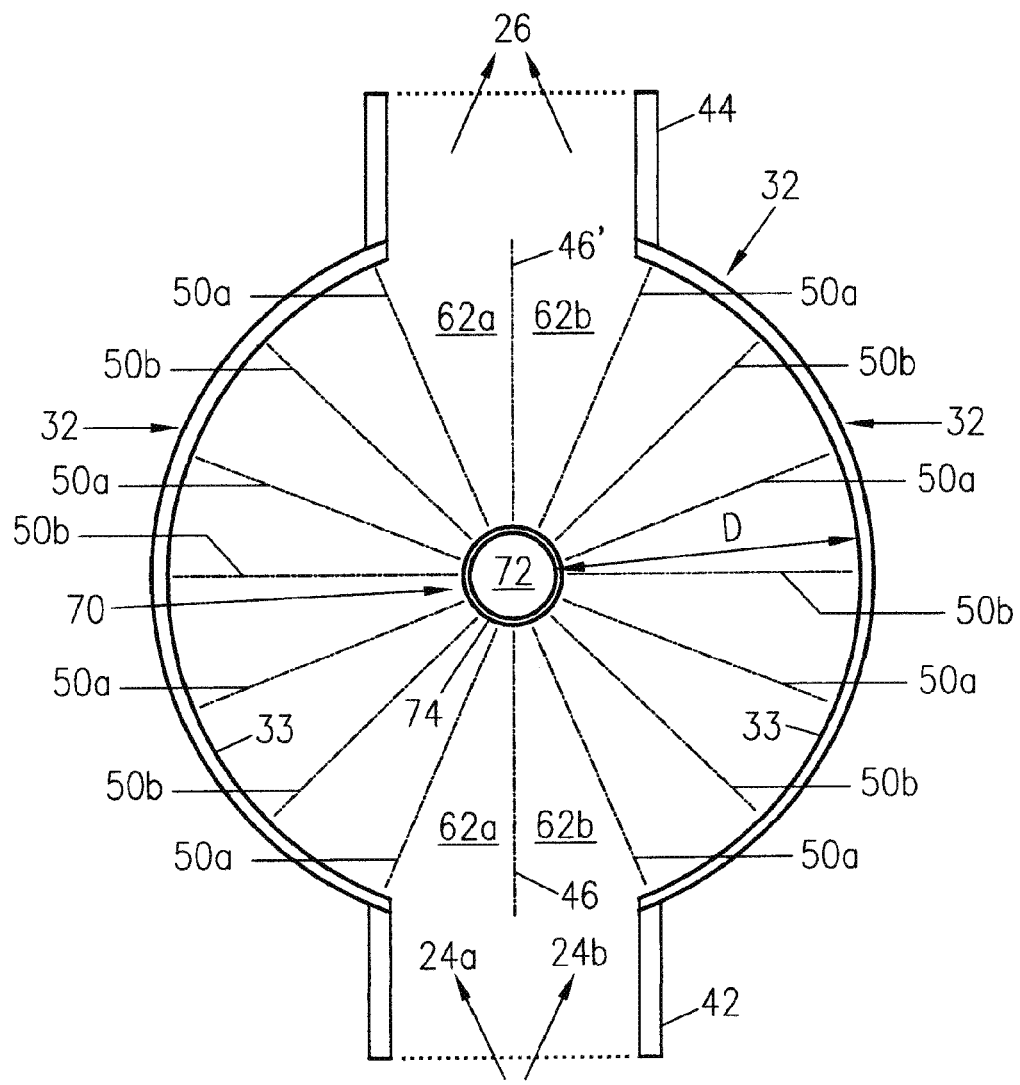
FIG. 5 is a cross-sectional view along the line 5-5 of FIG. 1.

A plurality of flow plates, or baffles 50, are circumferentially spaced about the container 30 (as best seen in FIG. 5), each one extending radially between the lamp's central sleeve 74 and the inside surface 33 of the container's outer wall 32. There are two types of flow baffles, a type "A" (identified by reference numerals 50a) and a type "B" (identified by reference numerals 50b) which are arranged in an alternating pattern between the inlet 42 and outlet 44. In the embodiment shown (FIGS. 4 to 8b) the type A and B baffles 50a, 50b are generally the same length (as measured along the longitudinal axis 22). A snug fit is provided between the inside edges 58a, 58b of the baffles 50a, 50b and the outer surface of the lamp sleeve 74, as well as between the outside edges 60a, 60b of the baffles and the inner surface 33 of the container's outer wall so as to minimize or eliminate fluid seepage past those interfaces. Although the top edge 52a of each of the type A baffles 50a abuts the lid 36 at the top end 34 of the container, the bottom edge 54a is spaced away from the end plate 40 to form an alternating series of openings 56a along the container's bottom end 38. Conversely, the bottom edge 54b of each of the type B baffles 50b abuts the container's bottom end 38, but the top edge 52b is spaced away from the lid 36 to form an alternating series of openings 56b along the container's top end 34.

Figure 6:
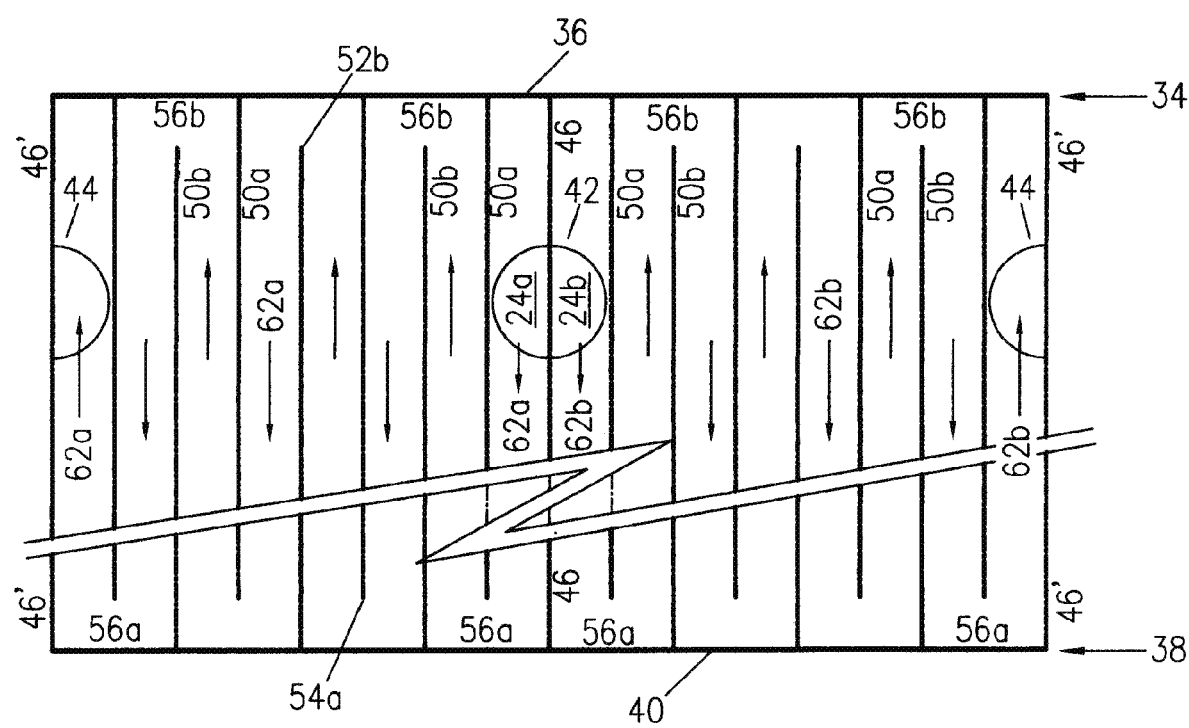
FIG. 6 shows the radial baffle arrangement of FIG. 5, as seen in an unfolded flat elevational view.

Hence, as best seen in FIG. 6, the circumferentially spaced arrangement of flow baffles 50a & 50b, coupled with the alternating arrangement of baffle openings 56a & 56b, creates two distinct meandering pathways 62a & 62b, or channels, oriented generally parallel to the longitudinal axis 22 and the UV lamp 72. The first pathway 62a accommodates and directs the fluid flow 24a from the inlet 42 to the outlet 44 in a generally clockwise manner about the axis 22, relative to the central lamp 72. The second pathway 62b likewise accommodates and directs the fluid flow 24b from the inlet 42 to the outlet 44 in a generally counter-clockwise manner about the axis 22, relative to the central lamp 72. Both pathways 62a & 62b terminate at the outlet 44 to allow the fluid flows 24a & 24b to converge and discharge from the reactor.

It will be appreciated that for a given size of container 30 and a given fluid flow volume, the circumferential spacing between each pair of flow baffles 50a & 50b will in part determine the fluid velocity through the container, namely a tighter spacing with more baffles will have greater fluid velocity than a more expansive spacing with fewer baffles. Fluid decontamination can also be influenced by the length L of the container, namely by augmenting or contracting the length of the fluid pathways 62a & 62b between the inlet and outlet. But length is determined during manufacture of the container and is effectively fixed thereafter, whereas the number of removably positioned flow baffles and their spacing can be altered at any time by a user to suit a particular operation, which is an advantage of the present invention.

Another desirable feature of this reactor design is the ability to control the exposure of the fluid streams 24a, 24b to the UV light emitted from the lamp 70. The wedge shaped channels (in plan view; FIG. 5) created between the flow baffles provides maximum opportunity of interaction of the radially emitted UV light with the meandering fluid being treated without shadowed areas, blind corners and such. In terms of sizing of the channels in the preferred embodiment, the cross-sectional area of each channel is made roughly equivalent to at least half the cross-sectional area of the inlet or outlet openings 42, 44 (the inlet and outlet openings are the same size in this instance) to at least accommodate each of the two fluid streams 24a, 24b without causing a flow restriction or back pressure. Likewise, each of the flow baffle openings 56a, 56b should at least be half the cross-sectional area of the inlet or outlet openings 42, 44 to accommodate each of the two fluid streams 24a, 24b.

The UV light reactor 20 of the present invention also incorporates photocatalytic materials to enhance the treatment of the incoming contaminated fluid stream 24. A Titanium Dioxide ($TiO_2$) coating has been found to be highly effective, although equivalent photocatalysts may be sufficiently suitable as well. The reactor design provides two particular advantages to the use of this photocatalyst. First, the reactor's specific baffle configuration optimizes internal surface area available for coating with the photocatalytic material. In the preferred embodiment the photocatalytic coating is provided on all surfaces of all flow baffles 50a, 50b, divider plates 46, 46[1], all inner surfaces 33 of the outer wall, on the inner surfaces of the top lid assembly 36 and bottom end plate 40, and inside the inlet and outlet connection areas. Second, this invention's wedge-shaped configuration also limits the maximum distance D of the photocatalytic coating from the source of UV light, to ensure unimpeded and effective coating-light interaction along the entire length of the pathways 62a & 62b, throughout the reactor. It has been found that a pre-set radial distance D of no more than about 75 mm maintains continuous optimal, namely substantially complete, activation of photocatalytic reactant by the UV light for effective treatment of the fluid. It appears that locating the coating further from the UV light source substantially decreases the coating's effectiveness in creating the desired amount, or concentration, of photocatalytic reactant, such as hydroxyl radicals which are considered powerful agents for sterilizing bacterial organisms and for oxidizing (aka "cracking") the chemical bonds of VOCs ("volatile organic compounds") in contaminated fluids.

The amount of surface area coated with photocatalytic reactant within a given size of container can be advantageously altered by employing removably positioned flow baffles. To illustrate, adding more flow baffles 50a, 50b to the container not only increases the length of the resultant flow paths 62a, 62b but adds surface area available for coating with photocatalytic material. Hence, the increased number of flow baffles should increase the amount of produced reactant, and thus increase the desirable interaction between the fluid and reactant along the also lengthened flow paths.

Figure 7:
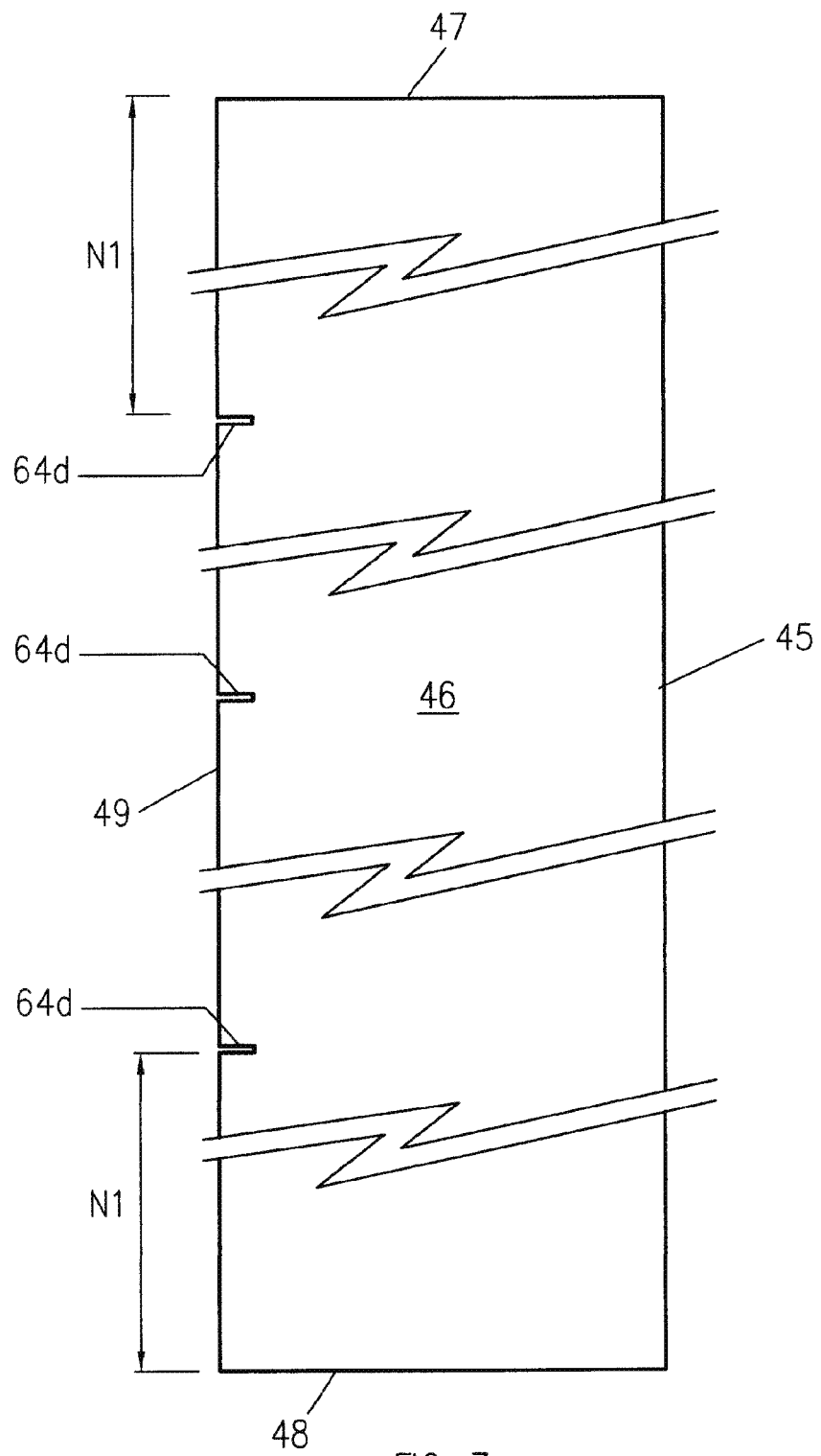
FIG. 7 is an elevational view of a divider plate shown in isolation.
Figure 8A:
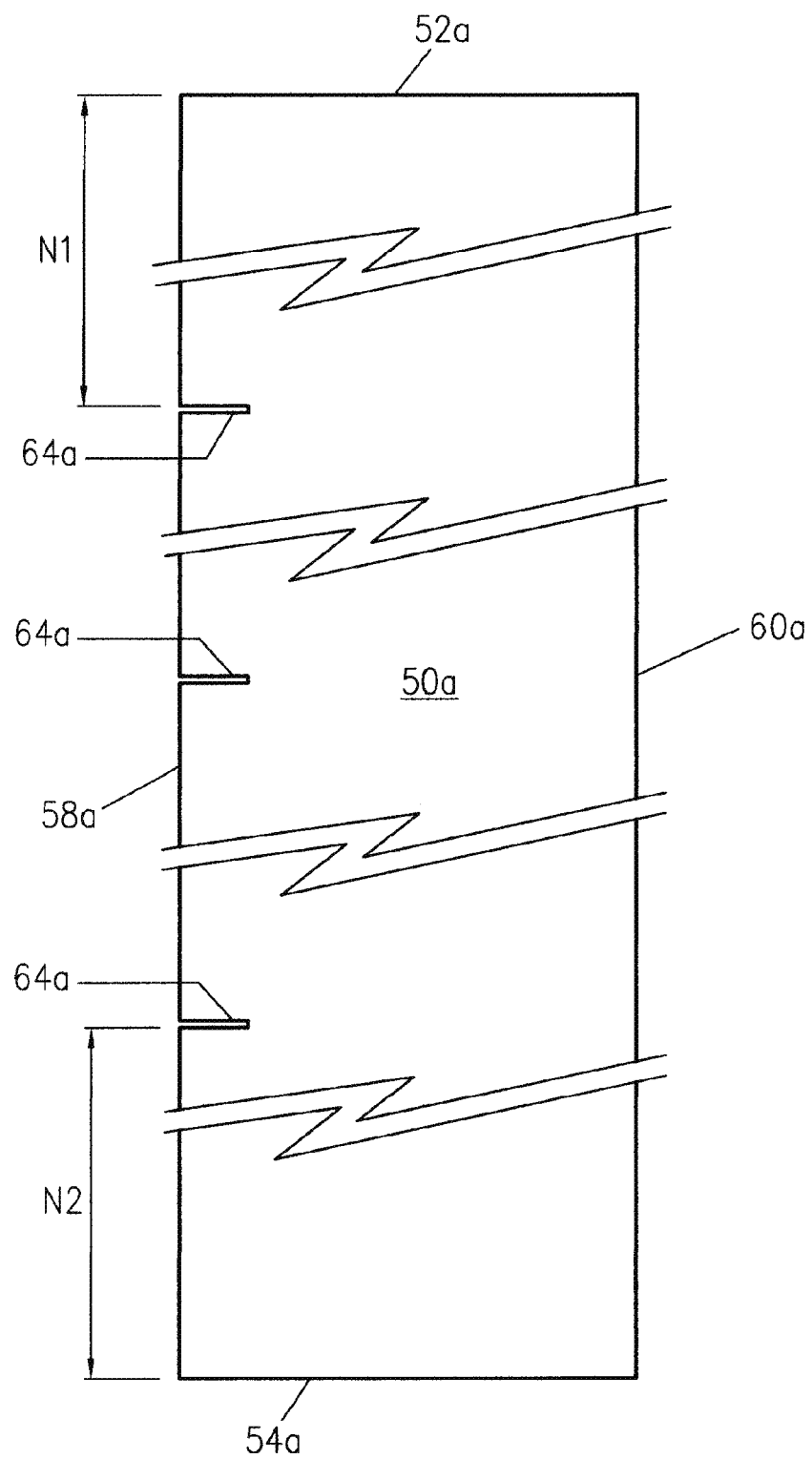
FIG. 8A is an elevational view of a flow baffle type A shown in isolation.
Figure 8B:
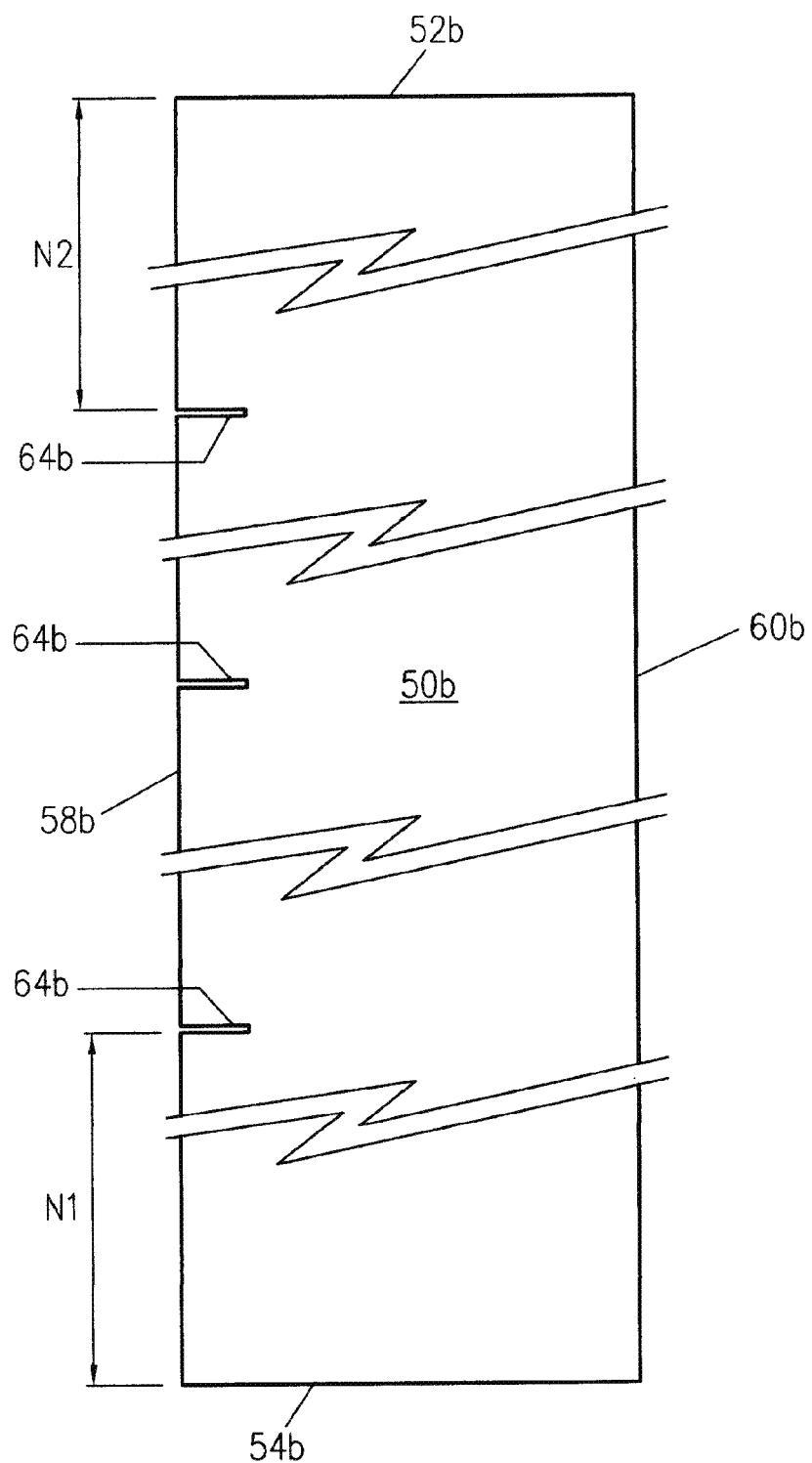
FIG. 8B is an elevational view of a flow baffle type B shown in isolation.
Figure 9:
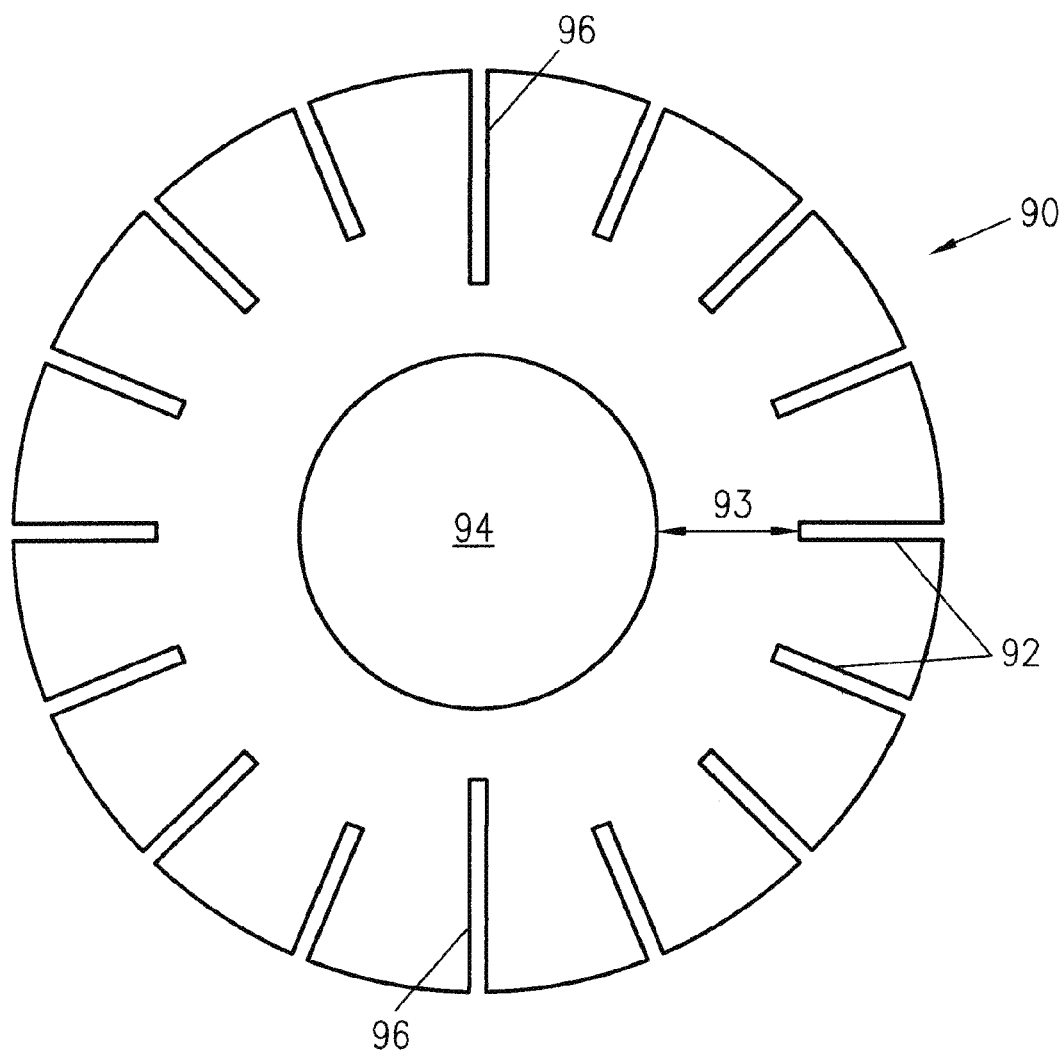
FIG. 9 is a plan view of a spacer ring shown in isolation for supporting the divider and flow baffles within the reactor as indicated in FIGS. 3 & 4.

FIGS. 7 to 9, in addition to FIGS. 4 and 5, show some specific aspects of the preferred embodiment's baffle design and arrangement. A typical flow baffle 50a shown in FIG. 8a has a series of notches 64a spaced along its inside edge 58a. Each notch 64a is positioned and sized to engage with one of several spacer plates, or rings, 90 in pre-set locations longitudinally along the length of the container 30, adjacent the lamp sleeve 74 (three locations are indicated in FIG. 3). Specifically, each baffle notch 64a fits through a corresponding ring slot 92 and radially inwardly over the adjacent spacer plate body 93. The notches and slots are sized to locate the baffle's inside edge 58a adjacent the lamp's sleeve 74 and the baffle's outside edge 60a adjacent the inner surface 33 of the container's outer wall 32 (as best seen in FIG. 5). The spacer ring's central opening 94 is sized to fit over the lamp sleeve 74. The flow baffles 50b shown in FIG. 8b have a similar structure with notches 64b adapted to engage the spacer ring slots 92 in much the same way. A prime difference between flow baffles A & B 50a, 50b is the notch offsets N1 and N2 from the baffles' top edges 52a, 52b and bottom edges 54a, 54b, respectively. For each flow baffle A the offset N1 is such that the top edge 52a abuts the container's top end 34 when inserted therein, and the offset N2 is such that the baffle's bottom edge 54a is spaced above the container's bottom end 38 when inserted therein to create the desired opening 56a between vertical flow channels. For flow baffle 50b essentially the opposite offsets N1 & N2 are provided so that the baffle's bottom edge 54b abuts the container's bottom end 38 when inserted therein, and the top edge 52b is spaced below the container's top end 34 when inserted therein to create the desired opening 56b between vertical flow channels. The reactor's two divider plates 46 (shown in FIG. 7) also have a series of shorter notches 64d for engaging the deeper dedicated slots 96 at radially opposed sides of the spacer rings 90, for locating the divider plates at the inlet 42 and outlet 44 to create and merge, respectively, the two fluid streams 24a, 24b as described earlier. Unlike the flow baffles A & B, the top and bottom notch off-sets are kept the same, namely at N1 in this example, so that the divider plate's top and bottom edges 47, 48 both abut the container's top and bottom ends 34, 38 respectively.

Assembly of the container's interior involves mating of the flow baffles 50a & 50b with each of the spacer rings 90 (three provided in the embodiment shown) as well as both divider plates 46 into the deeper slots 96 on opposed sides of the ring. The flow baffles 50a, 50b are arranged in an alternating pattern between the divider plates to form the basis of the meandering pathway described earlier. All inside edges 49, 58a, 58b of the divider and flow baffles should align with the edge of the spacer ring openings 94. This baffle and spacer ring assembly may then be inserted into the container 30 through an open top end 34 and placed onto the bottom end 38, such that the outside edges 60a, 60b, 45 of the flow baffles and the divider plates abut the container's outer wall 32. The bottom edges 48, 54b of the divider plates 46 and flow baffles "B" 50b should extend to the container's bottom end 38 whereas the bottom edge 54a of the other flow baffles "A" 50a should remain spaced above the bottom end plate to create the bottom openings 56a of the flow paths. Similarly, when the lid 36 is mounted on the container, the top edges 47, 52a of the divider plates 46 and flow baffles "A" 50a should extend to the container's top end 34 whereas the top edges 52b of the other flow baffles "B" 50b should remain spaced below the lid to create the top openings 56b of the flow paths. The lamp arrangement 70 may then be inserted through the lid's hole 37 and down the centre 22 of the container such that the lamp sleeve 74 abuts the spacer ring openings 94 and the inside edges 49, 58a, 58b of all the flow baffles and divider plates. Upon securing the lamp's mounting assembly 76 to the lid, the reactor 20 is ready for installation to inlet/outlet sources, and to a power source for controlling operation of the UV lamp.

The baffles of the present invention may be provided with a series of grooves or surface corrugations, such as a sinusoidal or crimped pattern, perpendicular to the central axis 22 across each baffle, thereby creating a 'washboard' effect and providing increased $TiO_2$ coated surface area exposure to UVC light. Other modified irregular baffle surface configurations could also be provided, such as dimples, cross-hatched corrugations, or longitudinal ripples (parallel to axis 22) along length of each baffle, but they are not preferred as they could reduce direct UV light contact with the $TiO_2$ coating due to shadow effect on the far side, of the dimples, ripples or cross-hatched corrugations.

In operation, the incoming contaminated fluid 24 at the container's inlet 42 is split by the exposed leading/outside edge 45 of the divider plate 46 into two streams 24a & 24b, which in the preferred embodiment should be substantially equal (FIG. 5). The left-hand stream 24a will then begin an extended journey next to the UV lamp assembly 70 by following the left-side meandering pathway 62a created by the arrangement of flow baffles 50a & 50b (best seen in FIG. 6). By the time the stream 24a has flowed clockwise from the inlet 42 to the outlet 44, it will have traveled about the equivalent of seven lengths of the container, parallel to its central axis 22. In addition, the fluid has a six fold greater exposure to coated surface area, as compared to a straight flow-through reactor design.

Throughout this travel in the new UV light reactor the fluid stream remains within a distance D of the lamp 70, which is preferably 75 mm or less. The counterpart right-hand stream 24b is subjected to the same travel criteria and benefits as the left-hand stream 24a. When both streams 24a & 24b arrive at the outlet 44, the fluid has been treated by the reactor and converges into a single discharge stream 26.

The reactor's lamp sleeve 74 requires periodic cleaning to avoid undue obstruction of UV light from the lamp into the container. This is easily achieved by merely suspending incoming fluid flow, disconnecting the lamp assembly from the lid 36 and removing it from the container via the lid hole 37. The sleeve may then be cleaned and the UV lamp inspected (and replaced if need be), and the lamp assembly can then be returned into the container as previously described, with minimal disruption to the operation of the reactor.

Many advantages, and further aspects and features, of the present invention may now be better understood.

For a given size of reactor, the flow path may be advantageously lengthened, or shortened if need be, by altering the number of flow baffles between the container's inlet and outlet, without altering the reactor's length L or other external dimensions. The same type of baffles can be used, but another set of spacer rings would be required with the desired number of slots 92 added and appropriately spaced circumferentially about the ring. An important added benefit of increasing the flow paths, by adding flow baffles, is the substantial increase in surface area coated with photocatalytic material, thereby increasing the production of desirable photocatalytic reactant to treat the fluid stream, along the now longer flow path. This "multiplied benefit" is not achieved in prior art devices for this purpose, with such ease, and without having to re-size or re-build the reactor.

The configuration of the reactor of the present invention advantageously positions and maintains a distance D of the UVC lamp to all $TiO_2$ coated surface areas inside the container to a maximum of about 75 mm, for sufficient, or "full", exposure of the coating to the UV light for substantially complete activation of photocatalytic reactant. It has been observed that within that distance D the photocatalytic reaction of UVC light with $TiO_2$ is most effective in creating hydroxyl radicals that are integral to sterilizing bacterial organisms and 'cracking' (oxidizing) chemical bonds of VOCs. Hydroxyl radicals appear capable of generating about one and a half times the oxidation power compared to the health hazard of Ozone ions. In addition, hydroxyl radicals are short lived (typically less than one second) and, by acting only as a catalyst, $TiO_2$ undergoes virtually no depletion during the photocatalytic process.

The configuration of the present reactor, with the inlet connection 42 placed diametrically opposite the outlet connection 44, allows for convenient joining of multiple UV light reactors 20, whether in sequence or in parallel, to efficiently achieve increased contaminated fluid volume treatment.

The use of UVC light and highly reactive $TiO_2$ photocatalyst, in combination with the baffle configuration of the present invention which provides increased fluid exposure time and coated surface areas, appears to effectively render biological organisms inert, and to convert virtually all hazardous and noxious aromatic contaminants (chemical compounds considered detrimental to health and the environment) into benign and substantially lesser harmful elements of carbon dioxide ($CO_2$) gas and water ($H_2O$) vapour. $CO_2$ and $H_2O$ already exist in the atmosphere as essential elements for the propagation of plant growth, and subsequently the generation of oxygen to sustain life. Thus, the comparatively small amount of $CO_2$ and $H_2O$ produced by the present invention can be considered environmentally beneficial rather than detrimental.

The present invention employs an 'Anatase $TiO_2$' photocatalytic coating on all baffle surfaces and inside enclosure surfaces (including inlet and outlet connections). In addition to having been designated physically and chemically safe and non-toxic, compared to other photo-catalysts, it is also cost effective, convenient to apply, easily activated and readily available. Although a 'Rutile $TiO_2$' photocatalytic coating could be used, it is not preferred because UVC light penetration is limited to about 2 nm. This is less desirable when compared to the approximately 5 nm UVC light penetration allowance by 'Anatase $TiO_2$', for greater hydroxyl radical generation.

The reactor can accommodate different types of energy sources, such UVV light, for treating different types of contaminants as desired. The UVV lamp could be used instead of the described combination of UVC lamp and $TiO_2$ coating, but a number of drawbacks must be considered. Use of a UVV lamp is generally not desired at this time as it is not as readily available as UVC lamps, is costlier than UVC lamps, and has only about one-tenth of the operating lifespan of a UVC lamp. Further, UVV light generates harmful ozone (a health hazard) which appears to have only about two-thirds the destructive energy of the hydroxyl radicals produced by the photocatalytic reaction of UVC light and $TiO_2$.

Finally, it is noted that energizing the preferred UVC lamp produces short wavelengths, approx. $\lambda$=254 nanometres (nm) long, capable of instigating immediate photocatalytic oxidation by reacting with the $TiO_2$ photocatalytic coating applied to the surface areas of the baffles and internal container surfaces. It seems this process creates the highly reactive hydroxyl radicals ($OH^-$) capable of not only destroying DNA and cell structures of biological organisms, but also chemical bonds associated with aromatic and toxic VOCs. Initial proof-of-concept testing, by subjecting the present reactor to a fluid flow of gaseous mixture consisting of benzene, toluene, ethylbenzene and xylene (jointly referred to as "BTEX"), achieved an average 96.7% destruction efficiency, 98.5% for Hydrogen Sulfide ($H_2S$), and 98.4% for Nitrogen Oxide Pollutants (NOx).

The above description is intended in an illustrative rather than a restrictive sense, and variations to the specific configurations described may be apparent to skilled persons in adapting the present invention to other specific applications. Such variations are intended to form part of the present invention insofar as they are within the spirit and scope of the claims below.

I claim:

1. An apparatus for treatment of a contaminated fluid comprising:
    a tubular housing having a length, top end, bottom end, and an outer wall fluidly sealed at each end, and having an inlet and an outlet, wherein said inlet receives said contaminated fluid and creates at least one fluid stream thereof;
    an elongated energy source for emitting energy, said elongated energy source having a center axis and being located centrally along the length of said tubular housing;
    a plurality of plates arranged in a spaced relationship to each other circumferentially about said elongated energy source,
        each of said plurality of plates being oriented radially between said elongated energy source and said outer wall of said tubular housing,
        each of said plurality of plates have a longitudinal axis parallel to the center axis of said elongated energy source,
        each plate abuts either said top or bottom end of the tubular housing,
        each plate defining an opening at one end thereof, wherein
        said openings in adjacent respective ones of said plurality of plates are located at opposed ends of said tubular housing thereby creating a meandering pathway between said ends of said tubular housing and parallel to said center axis of said elongated energy source for said fluid stream from said inlet to said outlet to provide uninterrupted exposure to energy emitted from said elongated energy source along a length of said meandering pathway wherein
        a direction of the meandering pathway on one side of each said respective plate is opposite to a direction of the meandering pathway on an opposite side of each said respective plate; and,
    a photocatalytic coating on at least one of said plurality of plates and inner surfaces of said outer wall of said tubular housing, wherein said inner surface of said outer wall of said tubular housing is within a pre-set radial distance of said elongated energy source for exposure to said energy to activate a photocatalytic reactant of said photocatalytic coating, so that said contaminated fluid flowing through said meandering pathway is continuously maintained within said pre-set radial distance to said elongated energy source and is provided adequate time flowing between said inlet and said outlet for combined exposure to said energy and said photocatalytic reactant to treat said fluid before exiting said tubular housing through said outlet.

2. The apparatus of claim 1 wherein said photocatalytic coating comprises Titanium Dioxide.

3. The apparatus of claim 1 wherein said elongated energy source comprises a lamp arrangement having an ultraviolet 'C' (UVC) light source.

4. The apparatus of claim 3 wherein said lamp arrangement includes a quartz sleeve to protect said ultraviolet 'C' (UVC) light source by preventing contact with said contaminated fluid.

5. The apparatus of claim 3 wherein said ultraviolet 'C' (UVC) light source includes a fitted clear sleeve surrounding said ultraviolet 'C' (UVC) light source to prevent injury if broken.

6. The apparatus of claim 1 wherein
    said inlet comprises a single aperture having a divider plate for splitting said incoming contaminated fluid into first and second fluid streams,
    said plates form distinct first and second pathways for said first and second fluid streams respectively,
    said first pathway is oriented clockwise about said center axis of said elongated energy source, and
    said second pathway is oriented counterclockwise about said center axis of said elongated energy source.

7. The apparatus of claim 6 wherein each of said two fluid streams accommodate substantially equal flows.

8. The apparatus of claim 6 wherein said inlet and outlet are located at radially opposed sides of said tubular housing.

9. The apparatus of claim 8 wherein said first and second fluid streams join at said outlet to provide a singular outflow of treated fluid from said enclosure through said outlet.

10. The apparatus of claim 1 wherein said plurality of plates are provided with surface corrugations oriented perpendicular to said axis of said elongated energy source.

11. The apparatus of claim 3 wherein said pre-set radial distance of said outer wall of said tubular housing from said lamp arrangement is no greater than 75 mm to maintain activation of said photocatalytic reactant by ultraviolet light for effective treatment of said fluid.

12. The apparatus of claim 11 wherein said plurality of plates are removably positioned within said tubular housing.

13. The apparatus of claim 10 wherein said plurality of plates are removably positioned within said tubular housing.

14. The apparatus of claim 1 wherein said plurality of plates are removably positioned within said tubular housing.

15. The apparatus of claim 1 wherein said elongated energy source further includes a central sleeve.

16. The apparatus of claim 1 further including a spacer plate or ring having a central opening sized to fit over said elongated energy source and an outer edge configured to engage and position respective ones of said plurality of plates.

17. The apparatus of claim 1 wherein each respective plate of said plurality of plates increase a length of said meandering pathway by a distance equal to a distance between said openings in adjacent respective ones of said plurality of plates whereby said length of said meandering pathway approximates a multiple of said length of said tubular housing.

18. The apparatus of claim 1 wherein said elongated energy source includes a mounting assembly which is removably secured to said end of said tubular housing.

19. The apparatus of claim 1 wherein a cross-sectional area of said meandering pathway between respective ones of said plurality of plates is at least one-half a cross-sectional area of said inlet or outlet.

20. The apparatus of claim 1 wherein a cross-sectional area of said openings in respective ones of said plurality of plates is at least one-half a cross-sectional area of said inlet or outlet.

* * * * *